US008673980B2

(12) United States Patent
Behnken et al.

(10) Patent No.: US 8,673,980 B2
(45) Date of Patent: Mar. 18, 2014

(54) CLOSTHIOAMIDES, COMPOSITIONS, AND METHODS FOR TREATING BACTERIAL OR FUNGAL INFECTIONS OR CANCER

(75) Inventors: Swantje Behnken, Jena (DE); Hans-Martin Dahse, Jena (DE); Christian Hertweck, Leipzig (DE); Keishi Ishida, Jena (DE); Thorger Lincke, Jena (DE); Martin Roth, Jena (DE); Florian Kloss, Jena (DE)

(73) Assignee: Leibniz-Institut fuer Naturstoff-Forschung und Infektionsbiologie, Jena (DE)

( * ) Notice: Subject to any disclaimer, the term of this patent is extended or adjusted under 35 U.S.C. 154(b) by 0 days.

(21) Appl. No.: 13/504,990

(22) PCT Filed: Nov. 2, 2010

(86) PCT No.: PCT/EP2010/006676
§ 371 (c)(1),
(2), (4) Date: Jun. 21, 2012

(87) PCT Pub. No.: WO2011/050994
PCT Pub. Date: May 5, 2011

(65) Prior Publication Data
US 2012/0270940 A1    Oct. 25, 2012

(30) Foreign Application Priority Data
Oct. 30, 2009  (EP) ................................ 09013674

(51) Int. Cl.
  *A01N 37/18*  (2006.01)
  *A61K 31/16*  (2006.01)
  *C07C 327/00*  (2006.01)
  *C07C 321/00*  (2006.01)
  *C07C 323/00*  (2006.01)
  *C07C 325/00*  (2006.01)
  *C07C 335/00*  (2006.01)
  *C07C 381/00*  (2006.01)
  *C07C 255/00*  (2006.01)

(52) U.S. Cl.
USPC ........... 514/599; 558/393; 560/251; 562/426; 564/74

(58) Field of Classification Search
None
See application file for complete search history.

(56) References Cited

PUBLICATIONS

Hayakawa et al. Thioviridamide, a novel apoptosis inducer in transformed cells from *Streptomyces olivoviridis*. J. Antibiot. 59(1): 1-5, 2006.*
Banala et al. Thioamides in nature: In search of secondary metabolites in anaerobic microorganisms. ChemBioChem, 2010, 11, 1335-1337, Jul. 5, 2010.*
Hill et al. Hot off the press. Nat. Prod. Rep. 2010, 27, 805-808.*
Abas et al. "Alkaloids from the Tunicate *Polycarpa aurata* from Chuuk Atoll" Journal of Organic Chemistry 1996 61(8) : 2709-2712.
Behling et al. "NMR, Mass Spectrometry and Chemical Evidence Reveal a Different Chemical Structure for Methanobactin that Contains Oxazolone Rings" Journal of the American Chemical Society 2008 130(38) : 12604-12605.
Brüggemann, H. and Gottschalk, G. "Comparative Genomics of Clostridia. Link Between the Ecological Niche and Cell Surface Properties" Annals of the New York Academy Sciences 2008 1125 : 73-81.
Brüggemann, H. and Gottaschalk, G. *Clostridia: Molecular Biology in the Post-genomic Era*. Chapter 1, Norwich, Great Britian, Caister Academic Press 2009, Print.
Desseyn et al. "The Characteristic Pattern of Thioamides in Infrared and Raman Spectra" Applied Spectroscopy 1978 32(1) : 101-105.
Fendri et al. "The Cellulosomes from *Clostridium cellulolyticum*. Identification of New Components and Synergies Between Complexes" The FEBS Journal 2009 276 : 3076-3086.
Frank et al. "Thioxylation as One-Atom-Substitution Generates a Photoswitchable Element within the Peptide Backbone" Angewandte Chemie International Edition 2000 39 (6) : 1120-1122.
Gannon et al. "Rhodamine Inhibitors of P-Glycoprotein: An Amide/Thioamide "Switch" for ATPase Activity" Journal of Medicinal Chemistry 2009 52 (10) : 3328-3341.
Hayakawa et al. "Structure of Thioviridamide, a Novel Apoptosis Inducer from *Streptomyces olivoviridis*" The Journal of Antibiotics 2006 59 (1) : 6-10.
Heap et al. "A Modular System for *Clostridium* Shuttle Plasmids" Journal of Microbiological Methods 2009 78 : 79-85.
Herold et al. "Cervimycin A-D: A Polyketide Glycoside Complex from a Cave Bacterium Can Defeat Vancomycin Resistance" Chemistry A European Journal 2005 11 : 5523-5530.
Kim et al. Methanobactin, a Copper-Acquisition Compound from Methane-Oxidizing Bacteria 2004 305 : 1612-1615.
Lincke et al. "Closthioamide: An Unprecedented Polythioamide Antibiotic from the Strictly Anaerobic Bacterium *Clostridium cellulolyticum*" Angewandte Chemie International Edition 2010 49 : 2011-2013.
Pan et al. "NonProtein Amino Acids from *Cycas revoluta*" Phytochemistry 1997 45 (3) : 517-519.
Parr et al. "Dihydrocaffeoyl Polyamines (Kukoamine and Allies) in Potato (*Solanum tuberosum*) Tubers Detected during Metabolite Profiling" Journal of Agricultural and Food Chemistry 2005 53 : 5461-5466.
Payot et al. "Metabolism of Cellobiose by *Clostridium cellulolyticum* Growing in Continuous Culture: Evidence for Decreased NADH Reoxidation as a Factor Limiting Growth" Microbiology 1998 144 : 375-384.
Payot et al. "Effect of Dilution Rate, Cellobiose and Ammonium Availabilities on *Clostridium cellulolyticum* Sporulation" Applied Microbiology and Biotechnology 1999 52 : 670-674.
Perret et al. "Use of Antisense RNA to Modify the Composition of Cellulosomes Produced by *Clostridium cellulolyticum*" Molecular Microbiology 2004 51 (2) : 599-607.
Reiner et al. "Effect of Thioxopeptide Bonds on α-Helix Structure and Stability" Journal of the American Chemical Society 2008 130 (25) : 8079-8084.

(Continued)

*Primary Examiner* — Anna Pagonakis
(74) *Attorney, Agent, or Firm* — Licata & Tyrrell P.C.

(57) ABSTRACT

This invention relates to the field of biologically active compounds and specifically to closthioamides, pharmaceutical compositions comprising these compounds, and their use as antibiotic, antifungal, and/or cytotoxic agent.

2 Claims, 2 Drawing Sheets

(56) References Cited

PUBLICATIONS

Tran et al. "Effects of Thioamide Substitutions on the Conformation and Stability of $\alpha$- and $3_{10}$-Helices" The Journal of the American Chemical Society 2002 124 (18) : 5222-5230.

Wang et al. "Mechanism of Thioamide Drug Action Against Tuberculosis and Leprosy" The Journal of Experimental Medicine 2007 204 (1) : 73-78.

* cited by examiner

CLOSTHIOAMIDES, COMPOSITIONS, AND METHODS FOR TREATING BACTERIAL OR FUNGAL INFECTIONS OR CANCER

This application is the national phase under 35 U.S.C. §371 of PCT International Application No. PCT/EP2010/006676, filed Nov. 2, 2010, which claims priority from EP 09013674.8, filed Oct. 30, 2009, the contents of which are incorporated herein by reference.

This invention relates to the field of biologically active compounds and specifically to closthioamides, pharmaceutical compositions comprising these closthioamides, and their use as antibiotic, antifungal, and/or cytotoxic agent.

Bacteria belonging to the genus *Clostridium* represent some of the most prominent microorganisms that lead an obligate anaerobic lifestyle. Clostridia occur in gastrointestinal tracts and are ubiquitously distributed in soil and sediments, rapidly decaying vegetation, and organic matter. Due to their potent catabolic properties, interest in these organisms has rapidly grown over the past years. Not only are clostridia routinely employed to degrade anthropogenic cellulosic waste products, they have also been increasingly exploited to meet the need for renewable chemicals and biofuels. On the other side, various pathogenic species produce the most powerful protein neurotoxins known to mankind, e.g. tetanus and botulinum toxins. Yet, apart from these protein neurotoxins, no secondary metabolites have been isolated from these or any other strictly anaerobic bacteria.

It is thought that anaerobes have a well regulated metabolism to avoid wasting their expensively produced energy for the production of molecules, e.g. secondary metabolites, which are not essential for their survival. Thus, the requisite biosynthesis gene clusters remain silent in the absence of environmental cues or particular triggers, as in many other microorganisms. In order to yield "cryptic natural products" external cues, co-cultivation and genomic approaches such as genome-mining, epigenetic remodeling, and engineered pathway activation have been employed.

Recently, genomes of *Clostridium* spp., e.g. *Clostridium kluyveri*, have been sequenced. *Clostridium cellulolyticum* (*C. cellulolyticum*; ATCC 35319) is another species of the genus *Clostridium* and its genome has been fully sequenced (GenBank accession NC_011898). *C. cellulolyticum* is an anaerobic nonruminal Gram-positive bacterium that has been isolated from decayed grass compost and is an important industrial strain due to its ability to degrade crystalline cellulose. So far, no secondary metabolite has been reported from *C. cellulolyticum*.

Effectiveness of known antibiotics is at a rapid decline. This is due to an emergence of an increasing number of resistant pathogens, e.g. multiresistant bacteria. Similarly, there is a rapid decline in the effectiveness of fungicides due to the emergence of resistance to many antifungal agents and with regard to cancer there hardly exist any effective therapies for its treatment. The discovery of novel compounds has become an increasing challenge. One of the most promising sources for novel antibiotics, fungicides or antitumor agents are microbial natural products. This is, because natural products own an element of structural complexity which is required for the inhibition of many protein targets in bacteria, fungi or vertebrates. Accordingly, there is a need for a constant supply of new antibiotics and fungicides to effectively treat bacterial and fungal infections as well as for novel compounds having antitumor activity.

Therefore, it is an object of the present invention to provide novel compounds having antibacterial, antifungal and/or antitumor activity. In particular, closthioamides are provided, especially a hitherto fully unprecedented type of polythioamide secondary metabolites from strictly anaerobic bacterium *C. cellulolyticum* (ATCC 35319).

The present invention relates to a compound (closthioamide) according to formula (I):

or a pharmacologically acceptable salt, solvate, hydrate or a pharmacologically acceptable formulation thereof, wherein $B^1$ is selected from cycloalkyl, heterocycloalkyl, alkylcycloalkyl, heteroalkylcycloalkyl, aryl, heteroaryl, aralkyl or heteroaralkyl, wherein said cycloalkyl, heterocycloalkyl, alkylcycloalkyl, heteroalkylcycloalkyl, aryl, heteroaryl, aralkyl or heteroaralkyl can be independently substituted with from 1 to 4 substituents which substituents are each independently selected from halogen atom, hydroxy, nitro, amino, cyano, mercapto, =O, =S, =NH, alkoxy, carboxyl, unsubstituted $C_1$-$C_6$alkyl, unsubstituted $C_2$-$C_6$alkenyl, unsubstituted $C_2$-$C_6$alkynyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl, unsubstituted $C_2$-$C_{11}$heteroaralkyl, sulfonyl, phosphoryl;

E is cyano, alkoxy, carboxyl, optionally substituted $C_1$-$C_6$alkyl, —CO—$R^1$, or a group represented by wherein
A is unsubstituted $C_1$-$C_{10}$ alkyl; and
G is a halogen atom, hydroxy, nitro, amino, cyano, mercapto, alkoxy, carboxyl, carboxamidyl group, —O—CO—$R^2$, or a group represented by wherein
$B^2$ is selected from cycloalkyl, heterocycloalkyl, alkylcycloalkyl, heteroalkylcycloalkyl, aryl, heteroaryl, aralkyl or heteroaralkyl, wherein said cycloalkyl, heterocycloalkyl, alkylcycloalkyl, heteroalkylcycloalkyl, aryl, heteroaryl, aralkyl or heteroaralkyl can be independently substituted with from 1 to 4 substituents which substituents are each independently selected from halogen atom, hydroxy, nitro, amino, cyano, mercapto, =O, =S, =NH, alkoxy, carboxyl, unsubstituted $C_1$-$C_6$alkyl, unsubstituted $C_2$-$C_6$alkenyl, unsubstituted $C_2$-$C_6$alkynyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl, unsubstituted $C_2$-$C_{11}$heteroaralkyl, sulfonyl, and phosphoryl;

$R^1$ is a hydrogen atom, a halogen atom, a hydroxy, a nitro, a cyano, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, and phosphoryl;

$R^2$ is an optionally substituted $C_1$-$C_8$alkyl; an optionally substituted $C_2$-$C_8$alkenyl, an optionally substituted $C_2$-$C_8$alkinyl, an optionally substituted heteroalkyl, an optionally substituted cycloalkyl, an optionally substituted heterocycloalkyl, an alkylcycloalkyl, a heteroalkylcycloalkyl, an optionally substituted aryl, an optionally substituted heteroaryl, an optionally substituted aralkyl, or an optionally substituted heteroaralkyl group; and $X^1$, $X^2$, and $X^3$ are each and independently of each other selected from O and S.

Compounds are generally described herein using standard nomenclature. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example, a chiral HPLC column.

Compounds herein may also be described using a general formula that includes variables such as, e.g., A, $B^1$, $B^2$, E, G, $R^1$, $R^2$, $R^3$, $R^4$, $X^1$, $X^2$, $X^3$ etc. Numbers as used herein, e.g., substituted with from 1 to 4 substituents, indicate integers, i.e. 1, 2, 3, 4 etc. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups and R* at each occurrence is selected independently from the definition of R*. Also, combinations of substituents and/or variables are preferably permissible only if such combinations result in stable compounds, i.e., compounds that can be isolated, characterized and tested for biological activity.

A "pharmaceutically acceptable salt" of a compound disclosed herein preferably is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 4, i.e., 0, 1, 2, 3, or 4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest, e.g. to a compound of formula (I) or a prodrug thereof. For example, a "ring substituent" may be a moiety such as a halogen, alkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. Moreover, the expression "substituted with from 1 to 3" or "substituted with 1 to 4 substituents" as used herein means that 1, 2, 3, or 4 substituents, preferably 1 or 2 substituents, more preferably 1 substituent is present at the respective group/molecular moiety that is substituted. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

The expression alkyl preferably refers to a saturated, straight-chain or branched hydrocarbon group that contains from 1 to 20 carbon atoms, preferably from 1 to 12 carbon atoms, more preferably from 1 to 6 carbon atoms, for example a methyl, ethyl, propyl, iso-propyl, n-butyl, iso-butyl, sec-butyl, tert-butyl, n-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, more preferably from 2 to 6 carbon atoms, for example an ethenyl, allyl, acetylenyl, propargyl, isoprenyl or hex-2-enyl group. Preferably, alkenyl groups have one or two, more preferably one, double bond(s) and alkynyl groups have one or two, more preferably one, triple bond(s).

The expression heteroalkyl preferably refers to an alkyl, alkenyl or alkynyl group, for example heteroalkenyl, heteroalkynyl, in which one or more, preferably 1, 2 or 3 carbon atoms have been replaced each independently of the others by an oxygen, nitrogen, phosphorus, boron, selenium, silicon or sulphur atom, preferably oxygen, sulphur or nitrogen. The expression heteroalkyl, for example, encompasses an alkoxy group. An alkoxy group denotes an alkyl group linked to oxygen thus: —O-alkyl. Furthermore, heteroalkyl preferably refers to a carboxylic acid or to a group derived from a carboxylic acid such as, for example, acyl, acylalkyl, alkoxycarbonyl, acyloxy, acyloxyalkyl, carboxyalkylamide, alkylcarbamoylalkyl, alkylcarbamoyloxyalkyl, alkylureidoalkyl, or alkoxycarbonyloxy.

Examples of heteroalkyl groups are groups of formulas —S—$Y^{a'}$-L, —S—$Y^{a'}$—CO—NR$^{a'}$R$^{b'}$, —$Y^{a'}$—NR$^{c'}$—CO—NR$^{a'}$R$^{b'}$, —$Y^{a'}$—NR$^{c'}$—CO—O—R$^{d'}$, —$Y^{a'}$—NR$^{c'}$—CO—R$^{d'}$, —$Y^{a'}$—NR$^{c'}$—CO—NR$^{a'}$R$^{b'}$, —$Y^{a'}$—NR$^{c'}$—CS—NR$^{d'}$-L, —$Y^{a'}$—O—CO—NR$^{a'}$R$^{b'}$, —$Y^{a'}$—CO—NR$^{a'}$R$^{b'}$, —O—$Y^{a'}$—CO—NR$^{a'}$R$^{b'}$, —$Y^{a'}$—NR$^{c'}$—CO-L, —$Y^{a'}$—O—CO—O—R$^{c'}$, —$Y^{a'}$—O—CO—R$^{c'}$, —$Y^{a'}$—O—R$^{c'}$, —$Y^{a'}$—CO-L, —$Y^{a'}$—NR$^{a'}$R$^{b'}$, R$^{c'}$—S—$Y^{a'}$—, R$^{a'}$—N(R$^{b'}$)—$Y^{a'}$—, R$^{c'}$—CO—$Y^{a'}$—, R$^{c'}$—O—CO—$Y^{a'}$—, R$^{c'}$—CO—O—$Y^{a'}$—, R$^{c'}$—CO—N(R$^{b'}$)—$Y^{a'}$—, R$^{a'}$—N(R$^{b'}$)—CO—$Y^{a'}$—, R$^{c'}$—SO—$Y^{a'}$—, R$^{c'}$—SO$_2$—$Y^{a'}$—, —$Y^{a'}$—NR$^{c'}$—SO$_2$—NR$^{a'}$R$^{b'}$, —$Y^{a'}$—SO$_2$—NR$^{a'}$R$^{b'}$, —$Y^{a'}$—NR$^{c'}$—SO$_2$—R$^{d'}$, R$^{a'}$—O—CO—N(R$^{b'}$)—$Y^{a'}$—, R$^{a'}$—N(R$^{b'}$)—C(=NR$^{d'}$)—N(R$^{c'}$)—$Y^{a'}$—, R$^{c'}$—S—CO—$Y^{a'}$—, R$^{c'}$—CO—S—$Y^{a'}$—, R$^{c'}$—S—CO—N(R$^{b'}$)—$Y^{a'}$—, R$^{a'-N(Rb')}$—CO—S—$Y^{a'}$—, R$^{c'}$—S—CO—O—$Y^{a'}$—, R$^{c'}$—O—CO—S—$Y^{a'}$—, R$^{c'}$—S—CO—S—$Y^{a'}$—; wherein R$^{a'}$ being a hydrogen atom, a $C_1$-$C_6$alkyl, a $C_2$-$C_6$alkenyl, a $C_2$-$C_6$alkynyl, or is joined to R$^{b'}$ to form a 4- to 10-membered cycloalkyl or heterocycloalkyl; R$^{b'}$ being a hydrogen atom, a $C_1$-$C_6$alkyl, a $C_2$-$C_6$alkenyl or a $C_2$-$C_6$alkynyl, or taken together with R$^{a'}$ to form a 4- to 10-membered cycloalkyl or heterocycloalkyl; R$^{c'}$ being a hydrogen atom, an optionally substituted $C_1$-$C_8$alkyl, an optionally substituted $C_2$-$C_8$alkenyl or an optionally substituted $C_r$$C_8$alkynyl; R$^{d'}$ being a hydrogen atom, optionally substituted $C_1$-$C_8$alkyl, optionally substituted $C_2$-$C_8$alkenyl or optionally substituted $C_2$-$C_8$alkynyl; L being a cycloalkyl, heterocycloalkyl, alkylcycloalkyl, heteroalkylcycloalkyl, optionally substituted aryl, optionally substituted heteroaryl, aralkyl, or heteroaralkyl; and $Y^{a'}$ being a bond, a $C_1$-$C_6$alkylene, a $C_2$-$C_6$alkenylene or a $C_2$-$C_6$alkynylene group. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, enol ether, dimethylaminomethyl, dimethylaminoethyl, acetyl, propionyl, butyryloxy, acetyloxy, methoxycarbonyl, ethoxycarbonyl, isobutyrylamino-methyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups. An example of a heteroalkylene group is a group of formulas —CH$_2$CH(OH)— or —CONH—.

The expression cycloalkyl preferably refers to a saturated or partially unsaturated cyclic group that contains one or more rings, preferably 1 or 2, containing from 3 to 14 ring carbon atoms, preferably from 3 to 10, more preferably 3, 4, 5, 6 or 7, ring carbon atoms. In an embodiment a partially unsaturated cyclic group has one, two or more double bonds, such as a cycloalkenyl group. Examples of a cycloalkyl group are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetralin, cyclopentylcyclohexyl, fluorocyclohexyl or cyclohex-2-enyl group.

The expression heterocycloalkyl preferably refers to a cycloalkyl group as defined above in which one or more, preferably 1, 2 or 3, ring carbon atoms have been replaced each independently of the others by an oxygen, nitrogen, silicon, selenium, phosphorus or sulphur atom, preferably oxygen, sulphur or nitrogen. A heterocycloalkyl group has preferably 1 or 2 ring(s) containing from 3 to 10, more preferably 3, 4, 5, 6 or 7, ring atoms. Examples are a piperidyl, piperazinyl, morpholinyl, urotropinyl, pyrrolidinyl, tetrahydrothiophenyl, tetrahydropyranyl, tetrahydrofuryl or 2-pyrazolinyl group and also a lactam, a lactone, a cyclic imide and a cyclic anhydride.

The expression alkylcycloalkyl preferably refers to a group containing both cycloalkyl and also an alkyl, alkenyl or alkynyl group in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10, preferably 3, 4, 5, 6 or 7, carbon atoms, and one or two alkyl, alkenyl or alkynyl groups having 1 or 2 to 6 carbon atoms, the cyclic groups being optionally substituted.

The expression heteroalkylcycloalkyl preferably refers to alkylcycloalkyl groups as defined above in which one or more, preferably 1, 2 or 3, carbon atoms have been replaced each independently of the others by an oxygen, nitrogen, silicon, selenium, phosphorus or sulphur atom, preferably oxygen, sulphur or nitrogen. A heteroalkylcycloalkyl group preferably contains 1 or 2 ring systems having from 3 to 10, preferably 3, 4, 5, 6 or 7, ring atoms, and one or two alkyl, alkenyl, alkynyl or heteroalkyl groups having from 1 or 2 to 6 carbon atoms. Examples of such groups are alkylheterocycloalkyl, heterocycloalkylalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being optionally substituted and saturated or mono-, di- or tri-unsaturated.

The expression aryl or Ar preferably refers to an aromatic group that contains one or more rings containing from 6 to 14 ring carbon atoms, preferably from 6 to 10, more preferably 6, ring carbon atoms. Examples are a phenyl, naphthyl, biphenyl, or anilinyl group.

The expression heteroaryl preferably refers to an aromatic group that contains one or more rings containing from 5 to 14 ring atoms, preferably from 5 to 10, more preferably 5 or 6, ring atoms, and contains one or more, preferably 1, 2, 3 or 4, oxygen, nitrogen, phosphorus or sulphur ring atoms, preferably O, S or N. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3"-bifuryl, 3-pyrazolyl and isoquinolinyl.

The expression aralkyl preferably refers to a group containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl, 1H-indene, tetralin, dihydronaphthalene, phenylcyclopentyl, cumene, cyclohexylphenyl, fluorene and indan. An aralkyl group preferably contains one or two aromatic ring systems, 1 or 2 rings, containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl preferably refers to an aralkyl group as defined above in which one or more, preferably 1, 2, 3 or 4, carbon atoms have been replaced each independently of the others by an oxygen, nitrogen, silicon, selenium, phosphorus, boron or sulphur atom, preferably oxygen, sulphur or nitrogen, that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems, 1 or 2 rings, containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 of those carbon atoms having been replaced each independently of the others by oxygen, sulphur or nitrogen atoms.

Examples of heteroaralkyl groups are aryloxy, arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl, heteroalkylheteroarylalkyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The expression "substituted" or "optionally substituted" as used herein in connection with any group refers to a group in which one or more hydrogen atoms have been replaced each independently of the others by fluorine, chlorine, bromine or iodine atoms or by OH, =O, SH, =S, NH$_2$, =NH, CN or NO$_2$ groups. Examples of substituted alkyl are 2,2,2-trichloroethyl or trifluoromethyl, and examples of substituted aryl (or substituted Ar) are 2-fluorophenyl, 3-nitrophenyl or 4-hydroxyphenyl. Examples of substituted cycloalkyl are, for example, fluorocyclohexyl and cyclic ketones such as, for example, cyclohexanone, 2-cyclohexenone or cyclopentanone. The expression "substituted" refers furthermore to a group in which one or more hydrogen atoms have been replaced each independently of the others by an unsubstituted $C_1$-$C_6$alkyl, unsubstituted $C_2$-$C_6$alkenyl, unsubstituted $C_2$-$C_6$alkynyl, unsubstituted $C_1$-$C_6$heteroalkyl, unsubstituted $C_3$-$C_{10}$cycloalkyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl or unsubstituted $C_2$-$C_{11}$heteroaralkyl group.

The expression "halogen" or "halogen atom" as preferably used herein means fluorine, chlorine, bromine, iodine.

As used herein a wording defining the limits of a range of length such as, e.g., "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

As used herein taking two substituents together to form a part of a cycloalkyl, a heterocycloalkyl, an alkylcycloalkyl, a heteroalkylcycloalkyl, an aryl, a heteroaryl, an aralkyl or a heteroaralkyl group means that a pair of adjacent substituents, e.g. $R^1$ and $R^2$, $R^2$ and $R^3$, or $R^7$ and $R^8$, etc., become ring members of a carbocyclic or heterocyclic ring moiety that is formed by said pair of adjacent substituents.

Preferably, the compound of the present invention is a compound (dosthioamide) of the general formula (II):

(II)

or a pharmacologically acceptable salt, solvate, hydrate or a pharmacologically acceptable formulation thereof, wherein A is a $C_1$-$C_{10}$ alkyl; and $B^1$ and $B^2$ are each and independently of each other selected from cycloalkyl, heterocycloalkyl, alkylcycloalkyl, heteroalkylcycloalkyl, aryl, heteroaryl, aralkyl or heteroaralkyl, wherein said cycloalkyl, heterocycloalkyl, alkylcycloalkyl, heteroalkylcycloalkyl, aryl, heteroaryl, aralkyl or heteroaralkyl can be independently substituted with from 1 to 4 substituents which substituents are each independently selected from halogen atom, hydroxy, nitro, amino, cyano, mercapto, =O, =S, =NH, alkoxy, carboxyl, unsubstituted $C_1$-$C_6$alkyl, unsubstituted $C_2$-$C_6$alkenyl, unsubstituted $C_2$-$C_6$alkynyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl, unsubstituted $C_2$-$C_{11}$heteroaralkyl, sulfonyl, phosphoryl, anticalins, antibodies, folic acid, fluorescence dyes or labels, and molecular probes.

The present invention preferably relates to a compound, wherein $B^1$ and/or $B^2$ is/are each and independently of each other selected from aryl or heteroaryl, wherein the aryl or heteroaryl can be independently substituted with from 1 to 4 substituents which substituents are each independently selected from halogen atom, hydroxy, nitro, amino, cyano, alkoxy, carboxyl, unsubstituted $C_1$-$C_6$alkyl, sulfonyl, and phosphoryl.

Further preferred is a compound of formula (I) or (II), wherein $B^1$ and/or $B^2$ is/are each and independently of each other selected from phenyl or 5-6 membered heteroaryl, wherein the phenyl or 5-6 membered heteroaryl can be independently substituted with from 1 to 4 substituents which substituents are each independently selected from halogen atom, hydroxy, nitro, amino, cyano, alkoxy, carboxyl, and unsubstituted $C_1$-$C_6$alkyl.

Preferably, in the compound of formula (I) or (II) $B^1$ and/or $B^2$ is/are phenyl or 5-6 membered heteroaryl, wherein the phenyl or 5-6 membered heteroaryl can be independently substituted with from 1 to 4 substituents which substituents are each independently selected from halogen atom, hydroxy, nitro, amino, cyano, alkoxy, carboxyl, and unsubstituted $C_1$-$C_6$alkyl.

Further preferred is a compound of formula (I) or (II), wherein $B^1$ and/or $B^2$ is/are phenyl or 6 membered heteroaryl, wherein the phenyl or 6 membered heteroaryl can be independently substituted with from 1 to 3 substituents which substituents are each independently selected from halogen atom, hydroxy, nitro, amino, cyano, alkoxy, carboxyl, and unsubstituted $C_1$-$C_6$alkyl.

Especially preferred is a compound of formula (I) or (II), wherein $B^1$ and/or $B^2$ is/are phenyl, wherein the phenyl can be independently substituted with from 1 to 3 substituents which substituents are each independently selected from halogen atom, hydroxy, nitro, amino, cyano, alkoxy, carboxyl, and unsubstituted $C_1$-$C_6$alkyl.

Also preferred is a compound of formula (I) or (II), wherein $B^1$ is represented by and/or $B^2$ is represented by wherein $R^3$ and $R^4$ are independently selected from a hydrogen atom, a halogen atom, a hydroxy, a nitro, a cyano, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, and phosphoryl.

Particularly preferred is a compound of formula (I) or (II), wherein $B^1$ and/or $B^2$ is/are hydroxyphenyl.

Preferably, in the compound of formula (I), E is cyano or carboxyl.

Also preferred is a compound of formula (I), wherein E is a group represented by wherein A is unsubstituted $C_1$-$C_{10}$ alkyl; and G is a hydroxy, nitro, amino, carboxyl group, or —O—CO—$R^2$, wherein $R^2$ is an optionally substituted methyl, ethyl, propyl, isopropopyl, n-butyl, iso-butyl, sec-butyl, tert-butyl, n-pentyl, n-hexyl, 2,2-dimethylbutyl or n-octyl group.

Also preferred is a compound of formula (I), wherein E is a group represented by wherein A is unsubstituted $C_1$-$C_{10}$ alkyl; and G is a group represented by wherein $X^1$ and $X^2$ are each and independently of each other selected from O and S, and $X^3$ is S.

Preferably, A is —$CH_2$—$CH_2$—, or —$CH_2$—$CH_2CH_2$— in the compound of formula (I).

Further preferred is a compound of formula (II), wherein A is —$CH_2$—$CH_2$—$CH_2$—.

It is to be noted that the present invention also encompasses all possible combinations of all preferred embodiments.

Particularly preferred, the compound of formula (I) is selected from one of the following structures:

Especially preferred, the compound of formula (I) or (II) has the following structure:

The compound of formula (I) or (II) can also be conjugated to an anticalin, antibody, folic acid, fluorescence dye or label, or molecular probe.

Closthioamide derivatives provided herein exhibit antitumor activity on cultured human tumor cell lines, i.e. an antiproliferative activity with an inhibition constant ($IC_{50}$) of preferably less than 1 µg/ml. Additionally, the closthioamide derivatives according to the present invention exhibit high antimicrobial activity, i.e. antibacterial activity and/or antifungal activity, with an inhibition constant ($IC_{50}$) of preferably less than 1 µg/ml The activity and more specifically the pharmacological activity of the closthioamide compounds according to the present invention can be assessed using appropriate in vitro assays. For instance, the $IC_{50}$ values of the compounds according to the present invention may be determined via a cytotoxic assay of cell growth. Preferred compounds of the invention have an $IC_{50}$ (half-maximal inhibitory concentration) of about 5 µg/ml or less, still more preferably an $IC_{50}$ of about 1 µg/ml or less, or even 0.5 µg/ml or less, even more preferably an $IC_{50}$ of about 0.1 µg/ml or less, or even 10 ng/ml or less in the assays mentioned above.

The therapeutic use of the compounds of the present invention their pharmacologically acceptable salts, prodrugs, solvates and hydrates and also formulations and pharmaceutical compositions containing the same are within the scope of the present invention. The present invention also relates to the use of those compounds of the present invention as active ingredient(s) in the preparation or manufacture of a medicament, especially, the use of compounds of formula (I) their pharmacologically acceptable salts, prodrugs or solvates and hydrates and also formulations and pharmaceutical compositions for the treatment of bacterial infections.

The pharmaceutical compositions according to the present invention comprise at least one compound of formula (I) and, optionally, one or more carrier substance(s), excipient(s) and/or adjuvant(s). Pharmaceutical compositions may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical compositions provided herein. For instance, the compounds of the invention may advantageously be employed in combination with an antibiotic, anti-fungal, or anti-viral agent, an-anti histamine, a non-steroidal anti-inflammatory drug, a disease modifying anti-rheumatic drug, a cytostatic drug, a drug with smooth muscle activity modulatory activity or mixtures of the aforementioned.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate.

For the preparation of such tablets, pills, semi-solid substances, coated tablets, dragées and hard gelatine capsules, the therapeutically usable product may be mixed with pharmacologically inert, inorganic or organic pharmaceutical carrier substances, for example with lactose, sucrose, glucose, gelatine, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat and polyols may be used. For the preparation of liquid solutions and syrups, pharmaceutical carrier substances such as, for example, water, alcohols, aqueous saline solution, aqueous dextrose, polyols, glycerol, vegetable oils, petroleum and animal or synthetic oils may be used. For suppositories, pharmaceutical carrier substances such as, for example, vegetable oils, petroleum, animal or synthetic oils, wax, fat and polyols may be used. For aerosol formulations, compressed gases that are suitable for this purpose, such as, for example, oxygen, nitrogen and carbon dioxide may be used. The pharmaceutically acceptable agents may also comprise additives for preserving and stabilising, emulsifiers, sweeteners, flavourings, salts for altering the osmotic pressure, buffers, encapsulation additives and antioxidants.

For the treatment of microbial or fungal infections as well as cancer, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day, about 0.5 mg to about 7 g per patient per day. The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination, i.e. other drugs being used to treat the patient, and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

Closthioamides provided herein are preferably administered to a patient such as, e.g., a human, orally or topically, and are present within at least one body fluid or tissue of the patient. Accordingly, the present invention further provides methods for treating patients suffering from microbial infections, i.e. bacterial or fungal infections, or cancer. In particular, the invention provides a method of preventing or treating a bacterial infection, fungal infection or cancer, said method comprising administering to a subject in need thereof an effective amount of at least one compound according to the invention. Preferably, the invention provides a method of preventing or treating a bacterial infection with methicillin-resistant *Staphylococcus aureus* (MRSA) or vancomycin-resistant *Enterococcus faecalis* (VRE).

As used herein, the term "treatment" encompasses both disease-modifying treatment and symptomatic treatment, either of which may be prophylactic, i.e., before the onset of symptoms, in order to prevent, delay or reduce the severity of symptoms, or therapeutic, i.e., after the onset of symptoms, in order to reduce the severity and/or duration of symptoms. Patients may include but are not limited to primates, especially humans, domesticated companion animals such as dogs, cats, horses, and livestock such as cattle, pigs, sheep, with dosages as described herein.

It is also within the present invention that the compounds according to the invention are used as or for the manufacture of a diagnostic agent, whereby such diagnostic agent is for the diagnosis of the diseases and conditions which can be addressed by the compounds of the present invention for therapeutic purposes as disclosed herein.

Compounds of formula (I) or (II) can be attained by simple peptide coupling, either convergent or linear. This approach is commonly pursued in pharmaceutical research and development. In particular, the compounds of the present invention can be prepared in a number of ways well known to those skilled in the art of organic synthesis. For example, the compounds of the present invention can be synthesized according to the following reaction scheme 1, together with synthetic methods known in the art of synthetic organic chemistry, or variations thereon as appreciated by those skilled in the art.

Hünig's Base, DCM, rt; (ii) deprotection/acid formation, e.g. $H_2$, Pd(C) (1 mol %), MeOH, rt; (iii) peptide coupling, e.g. EDC, HOBt, DMF, rt (iv) deprotection/bis-ammonium hydrochlorid formation, e.g. 1. dioxane, HCl (1.7 M), 50° C., sonication 2.MeOH, 50° C., sonication, directly converted; (v) peptide coupling, e.g. DCC or EDC, HOBt, Hünig's Base or TEA, DMF, rt; (vi) thionation, e.g. Lawesson's reagent, pyridine, 100° C., >20 h.

Those skilled in the art of organic synthesis will recognize that starting materials and reaction conditions may be varied including additional steps employed to produce compounds encompassed by the present invention.

BRIEF DESCRIPTION OF THE FIGURES

FIG. 4. A Activity of synthetic closthioamide (1) using 4 bacterial test strains; from left to right: (1) *E. coli*, (2) *Mycobacterium vaccae*, (3) methicillin-resistant *Staphylococcus*

Reaction scheme 1:

R*: protective group
B, e.g. hydroxyphenyl
A, e.g. —CH₂CH₂CH₂—

All starting materials and reagents are of standard commercial grade, and are used without further purification, or are readily prepared from such materials by routine methods. The six step synthesis depicted in the above reaction scheme 1 can, for example, be carried out as follows: step (i) peptide coupling; e.g. EDC or DCC, HOBt, triethylamine (TEA) or

*aureus* (MRSA), (4) vancomycin-resistant *Enterococcus faecalis* (VRE). B Ciprofloxacin control. These tests confirmed that closthioamide is a highly active antibacterial agent, in particular against methicillin-resistant *Staphylococcus aureus*, and vancomycin-resistant *Enterococcus faecalis*, with only moderate cytotoxicity (data not shown).

DETAILED DESCRIPTION OF A PREFERRED EMBODIMENT OF THE INVENTION

Figure 1:
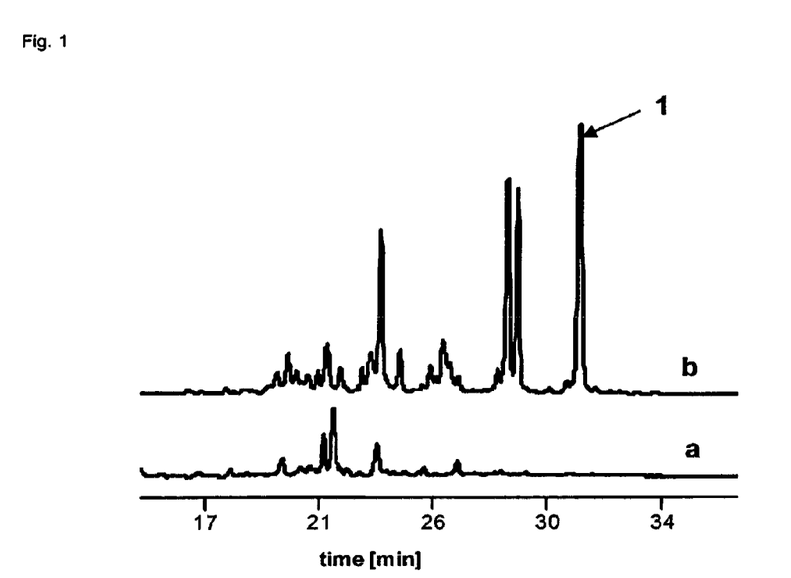
FIG. 1. HPLC profile of extracts from a *C. cellulolyticum* culture (a), and with supplemented with aqueous soil extract (b).

The major metabolite (1) was isolated from a 5 L culture and purified by sequential open column chromatography and RP-HPLC (FIG. 1), yielding 1.04 mg of a pale yellow compound. A preliminary bioactivity profiling revealed that 1 is cytotoxic against HeLa cells with an $IC_{50}$ of 5 μg mL$^{-1}$. Moreover, 1 has an antibacterial activity, in particular against gram positive bacteria, especially facultative anaerobic methicillin-resistant *Staphylococcus aureus* (MRSA) and vancomycin-resistant *Enterococcus faecalis*. According to HR-MS measurements, 1 has a molecular formula of $C_{29}H_{38}N_6O_2S_6$ and appeared to be amazingly rich in sulfur atoms. Furthermore, NMR data disclosed that the molecule is symmetrical: The $^{13}$C NMR and DEPT spectra indicated the presence of six methylene, two methine, and five quaternary carbons. In the $^1$H NMR spectrum signals corresponding to two olefinic and six methylene protons were observed (see Table 1).

TABLE 1

$^1$H NMR spectrum signals

| position | $\delta_C$ | $\delta_H$ (J [Hz]) |
|---|---|---|
| 1 | 27.1 | 1.94 |
| 2 | 44.1 | 3.62 (6.8, t) |
| 3 | 202.9 | — |
| 4 | 43.8 | 2.93 (6.8, t) |
| 5 | 45.8 | 4.01 (6.8, t) |
| 6 | 203.3 | — |
| 7 | 44.1 | 3.02 (6.8, t) |
| 8 | 46.5 | 4.09 (6.8, t) |
| 9 | 199.1 | — |
| 10 | 133.9 | — |
| 11 | 130.3 | 7.71 (6.8, dd) |
| 12 | 115.7 | 6.75 (6.8, dd) |
| 13 | 161.8 | — |

Figure 2:
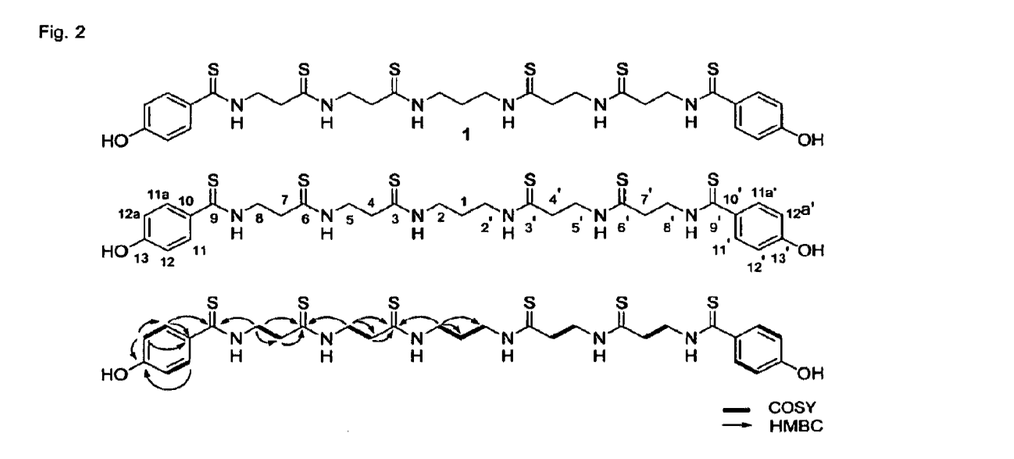
FIG. 2. Structure of closthioamide (1) and 2D NMR correlations.
Figure 3:
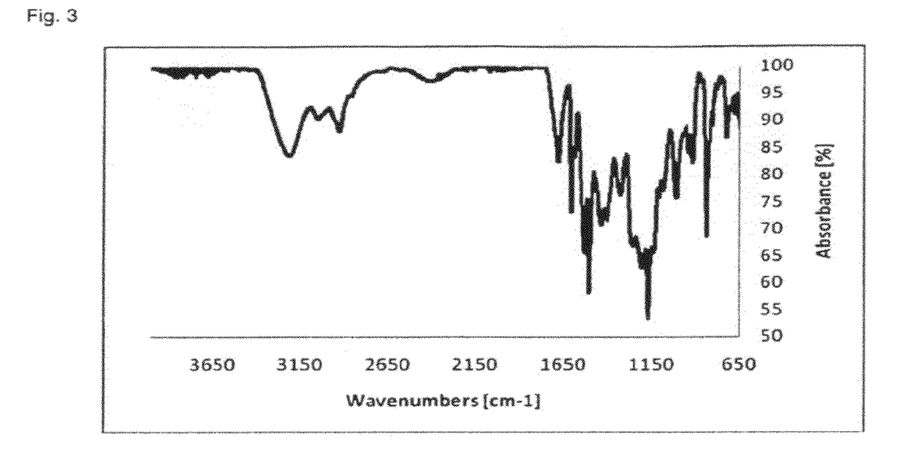
FIG. 3. IR spectrum of closthioamide (1).

The HMBC correlation between H2 (δ 3.62) and C2' (δ 44.1) confirmed the symmetrical structure of 1. Extensive $^1$H—$^1$H COSY, single-bond $^1$H—$^{13}$C HSQC and $^1$H—$^{13}$C longe-range HMBC analyses revealed one p-hydroxybenzoyl, one diaminopropane, and two β-alanine units. However, several lines of evidence excluded the possibility of a canonical amide linkage of these building blocks. Firstly, an amide carbonyl carbon shift would be expected at around 170 ppm. In stark contrast, the signals of the quaternary carbons C9 (δ 199.1), C6 (δ 203.3) and C3 (δ 202.9) are critically shifted to lower field. Secondly, the HR-MS data indicated the presence of six sulfur atoms in the molecule, and thus the chemical shifts clearly indicate that the sulfur atoms are incorporated into thioamide moieties (FIG. 2). This is also supported by intensive, characteristic $v_{cs}$ bands at 838 cm$^{-1}$ (H. O. Desseyn, B. J. van der Veken, M. A. Herman, *Appl. Spectr.* 1978, 32, 101-105) observed in the infrared spectrum of 1 (FIG. 3). In conclusion, the physicochemical data unequivocally revealed that 1 is a symmetrical polythioamide composed of a central diaminopropyl, four β-alanyl, and two terminal p-hydroxybenzoyl units.

Compound 1 is named closthioamide and is unique for the following reasons. Firstly, the symmetric (thio)amide structure is quite unusual. Related phenolic polyamine conjugates, some of them have a symmetrical structure (e.g. $N^1,N^{12}$-bis (dihydrocaffeoyl)spermine, kukoamine A), are only known from the plant kingdom (A. J. Parr, F. A. Mellon, I. J. Colquhoun, H. V. Davies, *J. Agric. Food. Chem.* 2005, 53, 5461-5466). Secondly, the six thioamide residues render 1 unique. Thioamide moieties are frequently employed in synthetic medicinal chemistry (F. Wang, R. Langley, G. Gulten, L. G. Dover, G. S. Besra, W. R. J. Jacobs, J. C. Sacchettini, *J. Exp. Med.* 2007, 204, 73-78; M. K. Gannon, J. J. Holt, S. M. Bennett, B. R. Wetzel, T. W. Loo, M. C. Bartlett, D. M. Clarke, G. A. Sawada, J. W. Higgins, G. Tombline, T. Raub, J., M. R. Detty, *J. Med. Chem.* 2009, 52, 3228-3241) and serve as isosters for amide bonds, lending higher rigidity and stability towards proteases (R. Frank, M. Jakob, F. Thunecke, G. Fischer, M. Schutkowski, *Angew. Chem., Int. Ed.* 2000, 39, 1120-1122; T. T. Tran, J. Zeng, H. Treutlein, A. W. Burgess, *J. Am. Chem. Soc.* 2002, 124, 5222-5230; A. Reiner, D. Wildemann, G. Fischer, T. Kiefhaber, *J. Am. Chem. Soc.* 2008, 130, 8079-8084). In stark contrast, thioamides are extremely scarce among naturally occurring organic compounds. Only four out of an estimated number of 170,000 known natural products feature thioamide groups: Cycasthioamide and (4-methoxyphenyl)-N-methyl-2-oxothioacetamide were isolated from a cycad, *Cycas revoluta*, (M. Pan, T. J. Mabry, J. M. Beale, B. M. Mamiya, *Phytochemistry* 1997, 45, 517-519) and a tunicate, *Polycarpa aurata*, (S. A. Abas, M. B. Hossain, D. van der Helm, F. J. Schmitz, M. Laney, R. Cabuslay, R. C. Schatzman, *J. Org. Chem.* 1996, 61, 2709-2712) respectively. The latter, however, could be an artefact byproduct from major component polycarpine. More recently, the unusual chalcophore methanobactin was reported as a metabolite of the methane-oxidizing bacterium *Methylosinus trichosporium*, (H. J. Kim, D. W. Graham, A. A. DiSpirito, M. A. Alternan, N. Galeva, C. K. Larive, D. Asunskis, P. M. Sherwood, *Science* 2004, 305, 1612-1615; L. A. Behling, S. C. Hartsel, D. E. Lewis, A. A. DiSpirito, D. W. Choi, L. R. Masterson, G. Veglia, W. H. Gallagher, *J. Am. Chem. Soc.* 2008, 130, 12604-12605) and thioviridamide was identified as a novel apoptosis inducer from *Streptomyces olivoviridis* (Y. Hayakawa, K. Sasaki, K. Nagai, K. Shin-ya, K. Furihata, *J. Antibiot* 2006, 59, 6-10). While a natural thioamide is rare, an entirely polythioamidated metabolite is totally unprecedented.

Finally, closthioamide 1 represents the first reported secondary metabolite from a *Clostridium* sp., and, to the best of our knowledge, even the first one from a strictly anaerobic microorganism in general.

The present invention is now further illustrated by the following examples from which further features, embodiments and advantages of the present invention may be taken.

However, these examples are by no means construed to be limiting to the present invention.

Example 1

Isolation and Characterization of Closthioamide

Bacterial Strain and Culture Conditions

The *Clostridium cellulolyticum* ATCC 35319 strain used in this study was originally isolated by Petitdemange et al. (1984) from decayed grass and was obtained from DSMZ GmbH (Braunschweig) as stock culture. It was grown anaerobically in serum glass bottles sealed with butyl rubber stoppers and an aluminium crimps at 37° C., without shaking, on modified complex medium CM3 (Payot et al. 1998) ($KH_2PO_4$ and $K_2HPO_4 \times 3\ H_2O$ were replaced by 3-(N-morpholino) propanesulfonic acid (10 g $l^{-1}$)) and supplemented with cellobiose (6 g $l^{-1}$) (Sigma-Aldrich, Schnelldorf). The anaerobic culture technique used was modified from that proposed by Hungate (1969) and Miller et al. (1974).

*C. cellulolyticum* was grown in batch culture in 1-liter fermentors (Biostat®Q, B. Braun Biotech International GmbH, Melsungen) with 800 ml of modified CM3 medium. Anoxic conditions were maintained by passing a stream of filter-sterilized nitrogen gas through the medium for ca. 3 h prior to inoculation and over the culture during fermentation. A 24 h-old glass-bottled culture was used as the inoculums (6.25% v/v). The cultures were stirred at 300 rpm at 37° C. and pH was controlled at 7.2 by automatic addition of 10% NaOH solution.

Variation of Culture Conditions to Induce Secondary Metabolite Production

In order to induce secondary metabolite production by *C. cellulolyticum* the following supplements and stress conditions were applied to 800 ml-fermentation cultures of *C. cellulolyticum* prior to inoculation: Carbon sources: cellulose MN300 (6 g $l^{-1}$), cellobiose (6 g $l^{-1}$), glucose (10 g $l^{-1}$), corn starch (6 g $l^{-1}$), corn steep (6 g $l^{-1}$), cellulose DS-0 (microcristalline, 6 g $l^{-1}$), cellulose powder from spruce (0.02-0.15 mm fibres, 6 g $l^{-1}$), cellobiose/arabinose (6 g $l^{-1}$/10 mg $l^{-1}$), dextrine (6 g $l^{-1}$), D(+)-mannose (6 g $l^{-1}$), D(-)-ribose (6 g $l^{-1}$), D(-)-fructose (6 g $l^{-1}$), D(+)-xylose (6 g $l^{-1}$), xylan from birch wood (6 g $l^{-1}$), cellobiose/corn steep extract (each 6 g $l^{-1}$), cellobiose/Avicel (6 g $l^{-1}$). Antibiotics: Kanamycin (10 µg $ml^{-1}$), Ampicillin (5 µg $ml^{-1}$). Osmotic stress: NaCl (0.7 M), Sorbitol (1 M). Limitations: starvation (cellobiose 0.05 g $l^{-1}$), minimal medium (Guedon et al. 1999), Temperature stress: 42° C., 40° C. Heavy metal stress: $CrCl_3$ (0.1 mM), $FeSO_4$ (0.5 mM), $CuSO_4$ (5 mM), $PbSO_4$ (0.1 mM). pH stress: pH 6.0. Supplements: trans-ferulic acid (0.1 mM), 8 div. acyl homoserine lactones (0.5 µM), syringaldehyde (0.2 mM), vanilline (0.1 mM). For the induction of closthioamide production 8 ml of filter-sterilized aqueous soil extract (soil sample from northern Germany) were added to each 800 ml-fermentation prior to inoculation. Cultures were grown until the late stationary phase.

Culture Extraction, HPLC, and HPLC-MS Analysis 800 ml-bacterial cultures were extracted with one volume ethyl acetate. Analytical HPLC was performed on a Shimadzu HPLC system consisting of an autosampler, high pressure pumps, column oven and DAD. HPLC conditions: C18 column (Nucleosil 100 C18, 5 µm, 125×3 mm) and gradient elution (MeCN/0.1% TFA (H2O) 0.5/99.5 in 30 min to MeCN/0.1% TFA (H2O) 100/0, then 100% MeCN for 10 min, flow rate 0.9 mL min-1). For mass detection a HPLC-MS series of Agilent Technologies 1100 series with DAD, an electron spray ion source operating in negative mode and a quadrupole mass analyzer by using an Eclipse Plus $C_{18}$ column with an elution gradient [MeCN/0.1% $HCO_2H$ 10/90 5 min, in 15 min to MeCN/0.1% $HCO_2H$ 99.5/0.5]

Isolation and Structural Characterization

The fermentation culture was depletively extracted with ethyl acetate. The extract was dried over Na2SO4 and concentrated under reduced pressure. For separation the extract was solved in methanol and directly injected into the analytical RP-HPLC by using a Macherey-Nagel Nucleosil 100-5 HD C18 column with an elution gradient [MeCN/0.1% TFA 10/90 5 min, in 45 min to MeCN/0.1% TFA 99.5/0.5] and a flow rate of 1 ml/min. NMR spectra were measured on a Bruker Avance DRX500 in d-4-Methanol. Spectra were referenced to the residual solvent peak. HRESI-MS was conducted on a Bruker Daltonics micrOTOF-Q spectrometer with an electronspray ion source. UV spectrum was obtained on a Shimadzu UV-1800 spectrometer for spectroscopy. A Jasco Fourier Transform Infrared Spectrometer was used to measure the infrared spectra by using ATR technique. From 5 L of fermentation 1.07 mg of a pale yellow compound could be obtained.

Closthioamide 1

HR/ESI-MS: $[M+Na]^+=717.1245$, calculated for $C_{29}H_{38}O_2N_6{}^{23}Na_1{}^{32}S_6$ gave 717.1273

$UV_{\lambda max\ (MeOH)}$ 269 nm; 219 nm; 203 nm

IR $v(NH)$ 3218 $cm^{-1}$; $\delta(NH)$ 1327 $cm^{-1}$; $v(CN)$ 1503 $cm^{-1}$; $v(CS)$ 838 $cm^{-1}$.

Example 2

Isolation and Characterization of Closthioamides A to G

Similarly to Example 1, from 10 L of fermentation that were extracted with ethyl acetate and purified by open column chromatography and preparative HPLC, closthioamides A to G could be obtained.

Closthioamide A:

Closthioamide B:

C$_{29}$H$_{38}$N$_6$O$_3$S$_5$
Exact Mass: 678.1609
Mol. Wt: 678.9807
C, 51.30; H, 5.64; N, 12.38; O, 7.07; S, 23.61

By LC-ESI/MS detected ions of 677.16 [M-H]— of closthioamides A and B indicate that these compounds exchanged one sulfur to one oxygen compared to dosthioamide (compound 1 above). The HRMS analysis and the resulting molecular formulas C$_{29}$H$_{38}$O$_3$N$_6$S$_5$ confirmed this finding. $^1$H and $^{13}$C NMR spectra of dosthioamides A and B were very similar to those of 1 except for the presence of one amide carbonyl carbon at 169.9 ppm (C-11) and 173.9 ppm (C-8), respectively. By extensive $^1$H—$^1$H COSY, $^1$H—$^{13}$C HSQC, and $^1$H—$^{13}$C HMBC analysis of closthioamides A and B, the position of the carbonyl group could be verified. The HMBC correlations of H-9 (3.67 ppm), H-10 (2.42 ppm) and H-12 (3.07 ppm) to the carbonyl carbon C-11 (169.9 ppm) in closthioamide A and the coupling of H-9 (3.57 ppm), H-7 (2.64 ppm) and H-6 (4.00 ppm) to C-8 (173.9 ppm) in closthioamide B confirm this finding.

Closthioamide C:

C$_{18}$H$_{25}$N$_3$O$_3$S$_3$
Exact Mass: 427.1058
Mol. Wt: 427.6075
C, 50.56; H, 5.89; N, 9.83; O, 11.22; S, 22.50

Closthioamide D:

C$_{13}$H$_{15}$N$_3$OS$_2$
Exact Mass: 293.07
Mol. Wt: 293.41
C, 53.22; H, 5.15; N, 14.32; O, 5.45; S, 21.86

Closthioamide E:

C$_{16}$H$_{23}$N$_3$O$_2$S$_3$
Exact Mass: 385.10
Mol. Wt: 385.57
C, 49.84; H, 6.01; N, 10.90; O, 8.30; S, 24.95

Closthioamide F:

C$_{16}$H$_{21}$N$_3$O$_3$S$_3$
Exact Mass: 399.0745
Mol. Wt: 399.5544
C, 48.10; H, 5.30; N, 10.52; O, 12.01; S, 24.08

Closthioamide G:

C$_{13}$H$_{16}$N$_2$O$_3$S$_2$
Exact Mass: 312.06
Mol. Wt: 312.41
C, 49.98; H, 5.16; N, 8.97; O, 15.36; S, 20.53

The presence of 3 thioamide groups in closthioamide C, E, and F could be detected by HRMS and UV. Based on HRMS, a non-symmetrical structure with the following formula was proposed: closthioamide C (C$_{18}$H$_{25}$N$_3$O$_3$S$_3$), E (C$_{16}$H$_{23}$N$_3$O$_2$S$_3$) and F (C$_{16}$H$_{21}$N$_3$O$_3$S$_3$). The $^{13}$C NMR spectra of dosthioamides C, E, and F were very similar to closthioamide 1. Each p-hydroxy thiobenzoyl-β-thioalanyl-β-thioalanyl sequence was determined by 2D NMR spectral analysis. Moreover, the closthioamide F showed a carbonyl acid signal at 175.4 ppm and closthioamide E showed a hydroxy substituted carbon atom at 58.5 ppm. Closthioamide C revealed the presence of an acetate unit including a methyl group at 20.9 ppm and the carbonyl group at 173.0 ppm. Using HMBC, the carbonyl signal of the ester group of closthioamide C (C-2) could be linked to methylen protons of H-3 and to the methyl protons H-1. COSY correlations verified the connection of the hydroxy methylen protons (H-1) of closthioamide E to methylen protons H-2. HRMS indicated the presence of two sulfur atoms in closthioamide G and D, respectively. Additionally, the NMR data showed the presence of a phenol group and a carboxy group at 175.2 ppm (C-1) in dosthioamide G which could be linked to the methyl protons H-2 and H-3 by HMBC. Moreover, a nitril group at 119.3 ppm could be connected to methylen protons by HMBC in closthioamide D.

Example 3

Synthesis of Closthioamide and Derivatives Thereof

Closthioamide 1, difluorodosthioamide 2, and dicyclohexyloxyclosthioamide 3 were prepared according to the above reaction scheme 1. All starting materials and reagents are of standard commercial grade, and are used without further purification, or are readily prepared from such materials by routine methods. Specifically, in step (i) p-hydroxybenzoic acid, p-cyclohexyloxybenzoic acid, and p-fluorobenzoic acid, respectively, were each reacted with benzyl-protected β-alanine via conventional peptide coupling using carbodiimides (EDC, DCC) and hydroxybenzotriazole (HOBt) to yield benzamides 5a-c (Chx=cyclohexyl).

5a R = OH
5b R = OChx
5c R = F

Reagents and conditions for step (i): 5a: EDC, HOBt, triethylamine (TEA), DCM, rt, 42 h, 68%; 5b: DCC, HOBt, Hünig's Base, DCM, rt, 18 h, 97%; 5c: DCC, HOBt, Hünig's Base, DCM, rt, 23 h, 99%. In step (ii), the benzyl group of 5a-c was removed by Pd(C)-mediated hydrogenation in a methanolic suspension, yielding the corresponding acid 6a-c.

6a R = OH
6b R = OChx
6c R = F

Reagents and conditions for step (ii): 6a: H2, Pd(C) (1 mol %), MeOH, rt, 75 min, >99%; 6b: H2, Pd(C) (1 mol %), MeOH, rt, 3.5 h, >99%; 6c: H2, Pd(C) (1 mol %), MeOH, rt, 80 min, >99%. Bisamide 9 was prepared by coupling t-butoxycarbonyl (Boc)-protected β-alanine with 1,3-diaminopropane via conventional peptide coupling using EDC and hydroxybenzotriazole (HOBt) (step iii).

9

Reagents and conditions for step (iii): EDC, HOBt, DMF, rt, 22 h, 79%. Both Boc groups of 9 were readily cleaved in solution of hydrogen chloride in methanol (step (iv): 1. dioxane, HCl (1.7 M), 50° C., sonication, 1 h; 2.MeOH, 50° C., sonication, 2 h, directly converted) to afford the bis-ammonium chloride 10, which could be used for the following steps without further purification.

10

The hexamide backbone of dosamides (4a-c) was assembled through the fusion of two equivalents of acid 6a-c and one equivalent of bis-hydrochloride 10 (step v).

4a R = OH
4b R = OChx
4c R = F

Reagents and conditions for step (v): 4a: DCC, HOBt, TEA, DMF, rt, 21 h, 61%; 4b: EDC, HOBt, Hünig's Base, DMF, 30° C., 68 h, 89%; 4c: EDC, HOBt, Hünig's Base, DMF, rt, 19.5 h, 86%. Finally, closthioamide 1, dicyclohexyloxyclosthioamide 2 and difluorodosthioamide 3 were obtained by converting amides 4a-c to thioamides (step vi). Reagents and conditions for step (vi): 1: Lawesson's reagent, pyridine, 100° C., 50 h, 12%; 2: Lawesson's reagent, pyridine, closed vessel, 100° C., 23 h, 96%; 3: Lawesson's reagent, pyridine, closed vessel, 100° C., 22 h, 65%.

assays (Herold et al., *Chem. Eur. J.,* 2005), e.g. agar diffusion test. In particular, closthioamide 1 was tested for its inhibitory effect on cell growth of different bacterial strains and/or fungi. The tested microbes included *Bacillus subtilis, Staphylococcus aureus, E. coli, Pseudomonas aeruginosa, Staphylococcus aureus* MRSA, *Enterococcus faecalis* VRE, *Mycobacterium vaccae, Sporobolomyces salmonicolor, Candida albicans,* and *Penicillium notatum.* Closthioamide 1 showed activity against all of the tested microbes thereby confirming its high antibacterial and antifungal activity.

1 R = OH
2 R = OChx
3 R = F

Alternatively, closthioamide 1 was prepared in high yields by deprotecting dicyclohexyloxyclosthioamide 2 in a mixture of trifluoromethanesulfonic (TFMSA) acid and trifluoroacetic acid (TFA). Reagents and conditions: TFMSA in TFA (1 M), 0° C., 12 min, 93%.

Figure 4:
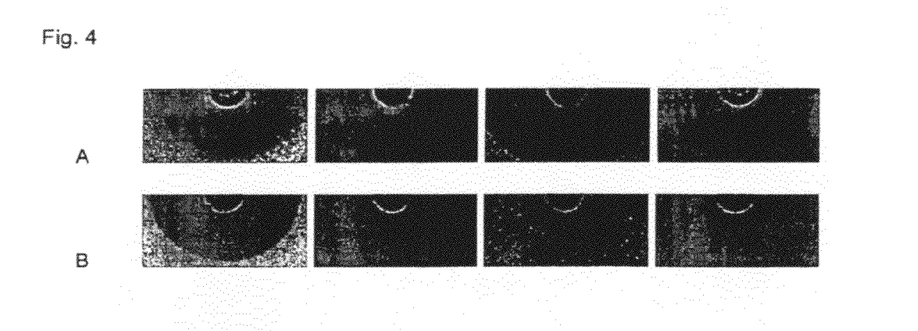

The activity of synthetic closthioamide 1 was shown to be equivalent to the activity of the bacterial metabolite; see FIG. 4A.

Example 4

Biological Activity 4.1. Determination of the Antiproliferative Activity of Closthioamide 1

For the detailed evaluation of its biological profile as anticancer agent, cultured human tumor cell lines were treated with the closthioamide 1. In particular, closthioamide 1 was tested for its inhibitory effect on cell growth of different human cell lines. The results are shown in Table 2.

TABLE 2

| | Antiproliferative activity $GI_{50}/CC_{50}$ [µg/mL] | | |
|---|---|---|---|
| Cell line | Origin | $GI_{50}$ | $CC_{50}$ |
| K-562 | Human erythromyeloblastoid leukemia cells | 1.5 | |
| HUVEC | Human umbilical vein endothelial cells | 6.4 | |
| HeLa | Human epithelial cervical cancer | | 5.1 |

4.2. Determination of Antimicrobial Activity

For the detailed evaluation of their antimicrobial (antibacterial, antifungal) activity, dosthioamides according to the invention were subjected to standardized antimicrobial Closthioamides A to G, and difluoroclosthioamide were tested for their inhibitory effect on cell growth of bacterial strains. The antibacterial activity of dosthioamides D to G was significantly reduced compared to that of closthioamide 1, closthioamides A to C, and difluorodosthioamide. In general, antibacterial activity correlated with the number of thioamide groups, where a reduced number of thioamide groups resulted in a reduced activity.

REFERENCES

H. Brüggemann, G. Gottschalk, Comparative Genomics of Clostridia, *Ann. N.Y. Acad. Sci* 2008, 1125, 73-81.

B H. Brüggemann, G. Gottschalk, Clostridia: Molecular Biology in the Post-genomic Era, *Caister Academic Press* 2009.

C J. T. Heap, O. J. Pennington, S. T. Cartman, N. P. Minton, A modular system for *Clostridium* shuttle plasmids, *J. Microbiol. Meth.* 2009, 78, 79-85.

D S. Perret, H. Maamar, J. P. Belaich, C. Tardif, Use of antisense RNA to modify the composition of cellulosomes produced by *Clostridium cellulolyticum, Mol. Microbiol.* 2004, 51(2), 599-607.

E S. Payot, E. Guedon, C. Cailliez, E. Gelhaye, H. Petitdemange, Effect of dilution rate, cellobiose and ammonium availabilities on *Clostridium cellulolyticum* sporulation, *Microbiol.* 1998, 144, 375-384.

F I. Fendri, C. Tardif, H. P. Fierobe, S. Lignon, O. Valette, S. Pages, S. Perret, The cellulosomes from *Clostridium cellulolyticum, FEBS J.* 2009, 276, 3076-3086.

T. Lincke, S. Behnken, K. Ishida, M. Roth and C. Hertweck, Closthioamide: an unprecedented polythioamide antibiotic from the strictly anaerobic bacterium *Clostridium cellulolyticum, Angew. Chem. Int. Ed.,* 2010, 49, 2011-2013.

K. Herold, F. A. Gollmick, I. Groth, M. Roth, K.-D. Menzel, U. M. Ilmann, U. Gräfe and C. Hertweck, Cervimycin A-D: A polyketide glycoside complex from a cave bacterium can defeat vancomycin resistance, *Chem. Eur. J.*, 2005, 11, 5523-5530.

The invention claimed is:

1. The compound closthioamide 1, wherein the structure of the compound is

2. A pharmaceutical composition comprising the compound of claim 1 and optionally, one or more carrier substance(s), excipient(s) and/or adjuvant(s).

* * * * *